(12) United States Patent
Tanzer et al.

(10) Patent No.: US 7,250,300 B2
(45) Date of Patent: Jul. 31, 2007

(54) METHOD AND MEANS FOR THE DETERMINATION OF TOTAL ACID

(75) Inventors: Dieter Tanzer, Ober-Ramstadt (DE); Uwe Krätschmer, Breuberg (DE)

(73) Assignee: Merck Patent GmbH, Darmstadt (DE)

( * ) Notice: Subject to any disclaimer, the term of this patent is extended or adjusted under 35 U.S.C. 154(b) by 382 days.

(21) Appl. No.: 10/491,425

(22) PCT Filed: Aug. 30, 2002

(86) PCT No.: PCT/EP02/09715

§ 371 (c)(1),
(2), (4) Date: Apr. 1, 2004

(87) PCT Pub. No.: WO03/029810

PCT Pub. Date: Apr. 10, 2003

(65) Prior Publication Data

US 2004/0203168 A1     Oct. 14, 2004

(30) Foreign Application Priority Data

Oct. 1, 2001 (DE) ................. 101 48 561

(51) Int. Cl.
*G01N 33/14* (2006.01)

(52) U.S. Cl. ............... 436/24; 436/20; 436/163; 426/15; 426/231

(58) Field of Classification Search ............. 422/56, 422/57, 61, 68.1, 75, 82.05; 436/20, 24, 436/163; 426/15, 231
See application file for complete search history.

(56) References Cited

U.S. PATENT DOCUMENTS

| | | | |
|---|---|---|---|
| 2,953,439 A | | 9/1960 | Elliott et al. |
| 3,811,837 A | | 5/1974 | Hoffman |
| 4,606,824 A | * | 8/1986 | Chu et al. .......... 210/635 |
| 5,853,669 A | * | 12/1998 | Wolfbeis ........ 422/82.05 |
| 6,071,515 A | * | 6/2000 | Mezes et al. ...... 424/130.1 |

FOREIGN PATENT DOCUMENTS

| | | |
|---|---|---|
| EP | 0184672 | 6/1986 |
| EP | 1248106 | 10/2002 |
| SU | 1097946 | 6/1984 |

OTHER PUBLICATIONS

Translation USSR Patent Specification No. SU1097946.*
http://www.medibix.com/runsearch.jsp?view=sku&product_1d=465276.*
Patent Abstracts of Japan vol. 013, No. 316 (P-900), Jul. 18, 1989 & JP 01086063 A (Toyo Roshi KK), Mar. 30, 1989.

* cited by examiner

*Primary Examiner*—Jan M. Ludlow
(74) *Attorney, Agent, or Firm*—Millen, White, Zelano, Branigan, P.C.

(57) ABSTRACT

The invention relates to a dry-chemical method and a test kit for the rapid, quantitative analysis of total acid in wine and must. In this method, a slightly alkaline buffer is added to the sample to be analyzed, and the total acid content is determined from the resultant pH with the aid of a test stick with pH indicator.

7 Claims, 1 Drawing Sheet

METHOD AND MEANS FOR THE DETERMINATION OF TOTAL ACID

Figure 1:
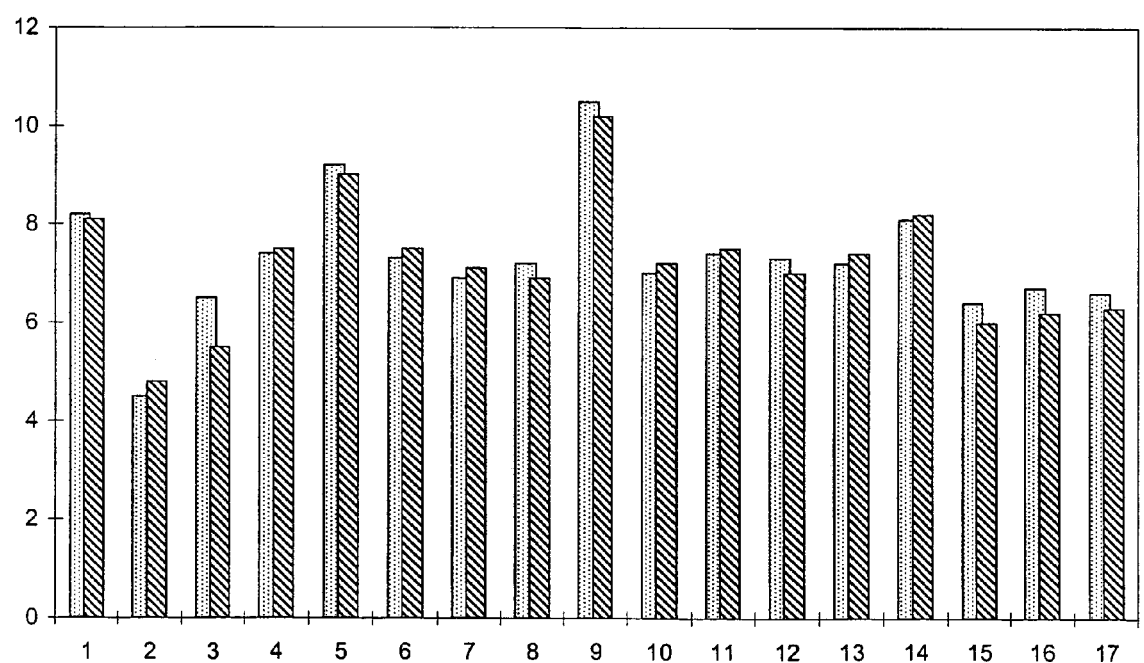

The invention relates to a dry-chemical method and test kit for the rapid, quantitative analysis of total acid in wine and must.

Wine of certified origin and quality has to meet certain requirements. Before a wine of this type can be put into circulation, it is analysed by specialised laboratories using prescribed analytical methods. In addition to this quality control at the end of the production process, the wine grower regularly has to check some important wine parameters between harvesting of the grapes and bottling of the wine in order to control the ripening process, prevent flavour flaws and precipitations, in short to achieve the desired quality.

Besides water and sugars, acids are the third principal component of a grape juice or must. The main acids in a healthy grape juice are malic acid (malate) and tartaric acid (tartrate), which are present in gram quantities. In addition, a multiplicity of further acids, such as, for example, citric acid (citrate) and succinic acid (succinate), occur in significantly lower quantities. Total acid represents the sum of all titratable acids. Carbonic acid is not included in total acid.

Total acid in musts can be subject to strong variations. In German musts, it is usually between 9 and 20 g/l, depending on the variety and ripeness. There is a direct correlation between the increase in the sugar content and the decrease in the acid content during grape ripening. The total acid content drops continuously during fermentation.

Since the total acid content exerts a significant influence on the flavour harmony of a wine, the wine grower endeavours to set an optimum acid content depending on the wine variety (usually about 5–9 g/l) by means of suitable treatment measures (for example biological or chemical acid degradation). In less good years, the musts, especially in more northern wine-growing countries such as Germany, contain more acid than is desirable for the flavour harmony of the wine. Conversely, the total acid content must not drop below limit values, some of which are prescribed. Thus, for example, table wine must have a total acid content of at least 4.5 g/l (Würdig G. and Woller R.: Chemie des Weines [Chemistry of Wine] (1989) Ulmer-Verlag, Stuttgart; Bergner K.-G. and Lemperle E.: Wein-kompendium [Wine Compendium] (1998), Hirzel-Verlag, Stuttgart; Schmidt A.: Aktuelle Weinanalytik [Modern Wine Analysis] (1983), Heller-Verlag, Schwäbisch-Hall).

The total acid content is therefore a very important monitoring parameter for the vintner and one which has to be determined regularly, quickly and reliably during wine cultivation and also as far as possible directly in the wine cellar.

According to the EC reference method, the total acid content is determined by potentiometric titration with an alkaline standard solution against pH 7. Outside the EC (for example in the USA and Australia), by contrast, titration with an alkaline standard solution against pH 8.2 is prescribed. The customary methods also employed by vintners do not determine the end point potentiometrically, but instead employ Bromothymol Blue as indicator for the end-point determination (Würdig G. and Woller R.: Chemie des Weines [Chemistry of Wine] (1989) Ulmer-Verlag, Stuttgart; Bergner K.-G. and Lemperle E.: Weinkompendium [Wine Compendium] (1998), Hirzel-Verlag, Stuttgart; Koch J.: Getränkebeurteilung [Beverage Analysis] (1986), Ulmer-Verlag, Stuttgart; Official Journal of the European Communities, Legislation, 1990). The latter procedure with visual end-point determination can be simplified if the caustic lye used for the titration is already coloured with bromothymol blue (blue lye). Commercial titration solutions and titration equipment matched to the titration make the determination easier for the vintner.

However, the procedure is still inconvenient, in particular for people without laboratory experience, and does not meet the demands made of a simple determination method. The recognition of the titration end point causes major difficulties, in particular in red wines owing to their inherent coloration. Thus, it is not surprising that different results are obtained in the potentiometric and visual methods (Lucan Z. D. and Palic A., Die Nahrung 38 (1994), 427–433). In addition, the consumption of titration agent (blue lye) is not inconsiderable (about 10–20 ml per titration) and is associated with disposal problems.

Analysis using solid, sorptive supports, so-called test sticks, has recently also increased in importance in wine analysis (Unger-Heumann M. and Tanzer D., G.I.T. Laboratory Journal 3 (1998), 174–175). The main advantages of these dry-chemical methods include, in particular, simple handling and straightforward disposal owing to the small amounts of reagent. All or the majority of the reagents necessary for the analysis reaction are embedded in corresponding layers of a solid, sorptive or swellable support, to which the sample is applied. The analysis reaction proceeds after contact of the reaction zone with the sample. The colour formed is a measure of the amount of analyte to be determined and can be evaluated visually, i.e. semi-quantitatively or quantitatively, using simple reflectometers.

However, it has hitherto not been possible to achieve a dry-chemical method for the determination of total acid.

The present invention therefore has the object of providing a method for the determination of total acid in must and wine which is simple and rapid to carry out, can thus also be carried out in the wine cellar, and is inexpensive. In particular, it should be possible to carry out the method according to the invention using not only semi-quantitative, visual evaluation, but also quantitative evaluation using a reflectometer.

It has been found that a simple and fast dry-chemical method for the determination of total acid in wine and must can be provided by firstly adding a slightly alkaline buffer solution to the sample, and determining the resultant change in pH using a test stick to which a suitable pH indicator has been applied.

The present invention relates to a method for the determination of total acid in must and wine, characterised by the following method steps:

a) provision of a test stick which has at least one pH indicator;
b) addition of an alkaline reagent solution to the sample to be analysed;
c) dipping of the test stick into the mixture from step b)
d) evaluation of the colour reaction on the test stick.

In a preferred embodiment, the alkaline reagent solution added in step b) is a tris(hydroxymethyl)aminomethane buffer.

In a further preferred embodiment, a test stick which comprises, as pH indicator, one or more of the indicators Bromocresol Green, Phenol Red, Bromophenol Red, Chlorophenol Red and curcumine is provided in step a).

In a preferred embodiment, a test stick which has two zones with different pH indicators is provided in step a).

In a preferred embodiment, the evaluation in step d) is carried out reflectometrically.

The present invention also relates to a test kit for the determination of total acid in must and wine at least comprising an alkaline reagent solution and a test stick with at least one pH indicator.

In a preferred embodiment, the test kit contains, as alkaline reagent solution, a tris(hydroxymethyl)aminomethane buffer.

In a further preferred embodiment, the test kit contains a test stick which has, as pH indicator, one or more of the indicators Bromocresol Green, Phenol Red, Bromophenol Red, Chlorophenol Red and curcumine.

In a preferred embodiment, the test kit contains a test stick which has two zones with different pH indicators.

FIG. 1 is explained in greater detail in Example 2.

In order to carry out the method according to the invention for the determination of total acid in must and wine, firstly a certain amount of reagent solution is added to the sample to be analysed. A test stick is then dipped briefly into the mixture consisting of must or wine and reagent solution, and the resultant colour reaction on the test stick is evaluated quantitatively with the aid of a reflectometer or semi-quantitatively by comparison with a colour card. On addition of the weakly alkaline reagent solution, the acids in the sample react with the reagent solution, accompanied by a change in the pH. This change, which is proportional to the acid content, is determined by means of pH indicators on the test stick.

For the purposes of the invention, the term "must and wine" denotes any aqueous sample which consists predominantly of unfermented, partially fermented or fermented grape juice, preferably grape juice or must, partially fermented must arising during wine cultivation, or wine. However, it is clear to the person skilled in the art that, given corresponding calibration, the method according to the invention can also be used to determine the total acid content in other juices or in fermented products obtained therefrom. Examples of such sample materials are fruit or vegetable juices, fruit wines or distillates of fermented products.

The alkaline reagent solution which is added to the sample is an alkaline buffer solution which effects a readily measurable pH change after addition to a defined amount of sample solution. Suitable buffer solutions are, for example, phosphate and triethanolamine buffers or buffers based on heterocyclic amines or derivatives or mixtures thereof. Examples of suitable buffer systems based on heterocyclic amines are imidazole, 1-methylimidazole, 2-methylimidazole, pyrazole, pyrimidine, pyridazine, piperazine, triazole and triazine buffers. Particular preference is given to an aqueous tris(hydroxymethyl)aminomethane buffer (TRIS buffer). The pH of the buffer solution must be in the range 9–12.5, particularly preferably in the range 9.5–10.5. The concentration of the buffer solution must be in the range of about 1 mmol/l–100 mmol/l, particularly preferably in the range 10–50 mmol.

Through specific matching of the concentration of the buffer, the amount of added buffer solution and the amount of sample solution, a pH change can be achieved, depending on the total acid content, which can be evaluated very reliably by means of test sticks.

The pH of a wine or must is in the region of about 3. The metering of buffer solution is set at such a rate that only a slight pH change takes place in the case of samples having high total acid contents and a large pH change which can be readily evaluated using test strips takes place in the case of samples having small total acid contents. The pH here should be shifted into the range between pH 4 and pH 12, preferably between pH 4 and pH 10.

On use of the preferred TRIS buffer, a solution of 2.4 g of tris(hydroxymethyl)aminomethane in 1 l of water, for example, is suitable for the determination of total acid contents between 1 and 14 g/l if 0.2 ml of a sample is added to 1 ml of the buffer solution. If the total acid content of the sample is greater than 14 g/l, the added amount of buffer solution should be increased (factor 1.2–2.0) for the same amount of sample or a somewhat more highly concentrated buffer (for example 0.05 mol/l instead of 0.02 mol/l) should be used or the amount of sample should be reduced (for example 0.1 ml of sample).

Suitable indicators on the test stick are in principle all colour indicators or mixtures of colour indicators whose spectral properties have a significant pH dependence in the pH range of about 4–12, preferably 4–10, to be investigated and can be evaluated visually or quantitatively by means of a reflectometer. Particularly advantageous indicators for the determination according to the invention have proven to be Bromocresol Green, Phenol Red, Bromophenol Red, Chlorophenol Red and curcumine and in particular mixtures of two or more of these indicators. Combination of analysis zones with different colour indicators, as usual in universal pH indicator papers, enables the analysis sensitivity to be further improved.

The indicators are typically located on the test strip in a sorptive support in which all further reagents necessary for the analysis (for example stabilisers and solubilisers) are also embedded. The sorptive support to which the analysis reagents are applied usually does not cover the entire test strip, but instead merely a zone of the test stick. In this way, it is possible not only to combine one zone having one composition of analysis reagents, but instead a plurality of zones having different compositions, for example for the analysis of different concentration ranges, on a test stick.

The sorptive supports used can be all materials which are usually in use for such tests. The most widespread is the use of filter paper, but it is also possible to employ other sorptive cellulose or plastic products.

The sorptive supports are impregnated in a known manner with impregnation solutions comprising the desired indicators, optionally stabilisers and solubilisers. The impregnated and dried papers may be cut to size in a suitable manner and adhesively bonded or heat-sealed to support films or foils in a known manner.

The present invention furthermore also relates to a test kit which contains at least one test stick with at least one pH indicator which is suitable for carrying out the method according to the invention, and at least one alkaline reagent solution. Suitable test sticks are those which have colour indicators or mixtures of colour indicators whose spectral properties have a significant pH dependence in the pH range of about 4–12, preferably 4–10, to be investigated and can be evaluated visually or quantitatively by means of a reflectometer.

A significant advantage for a test system is its long shelf life without change in the test properties (in particular calibration data). Storage experiments with the test system according to the invention show that the target storage time of a shelf life of at least 2 years under room-temperature conditions can be achieved without problems.

The method according to the invention and the test kit according to the invention thus offers for the first time the possibility of determining the total acid content of wine or must by means of a simple dry-chemical method. The addition according to the invention of a weakly alkaline buffer solution to the sample changes the pH of the sample, depending on the acid content, into a pH range which can be measured easily and reliably using the pH indicator test stick. The accuracy and sensitivity of the method according to the invention is comparable with potentiometric titration, which is significantly more complex.

Even without further comments, it is assumed that a person skilled in the art will be able to utilise the above description in its broadest scope. The preferred embodiments and examples should therefore merely be regarded as descriptive disclosure which is absolutely not limiting in any way.

The complete disclosure content of all applications, patents and publications mentioned above and below, and of the corresponding application DE 101 48 561.1, filed on 01 Oct. 2001, are incorporated into this application by way of reference.

EXAMPLES

Example 1

Determination of Total Acid Using Test Sticks—Reflectometric Evaluation of the Reaction Colour:

Production of the Test Sticks:

The following impregnation solutions are applied to filter papers (Binzer, 1450 CV; acid-washed) and then dried using warm air. The papers are heat-sealed to a white support film using hot-melt adhesive (for example Dynapol® 1272 adhesive) and cut into strips in a suitable manner so as to give reaction zones of about 6 mm×8 mm.

Compositions of the Impregnation Solutions:

For Total Acid Measurement Range About 1–8 g/l:

In each case 0.1% alcoholic solutions of Bromophenol Red (22 g), Phenol Red (87 g), curcumine (130 g) and 260 g of ethanol are weighed out successively into a 1 l conical flask.

For Total Acid Measurement Range About 7–14 g/l:

In each case 0.1% alcoholic solutions of Bromocresol Green (125 g) and Chlorophenol Red (375 g) are weighed out into a 1 l conical flask.

Preparation of the Buffer Solution:

0.24 g of tris(hydroxymethyl)aminomethane are dissolved in 100 ml of deionised water with stirring.

Analysis:

1 ml of the buffer solution is added to 0.2 ml of sample (wine or must). For the determination, the test sticks are dipped briefly into the sample solution so that they are completely wetted. Depending on the total acid content of the sample and the resultant pH, the colour indicators change colour within a few seconds. For quantitative evaluation, the test strips are evaluated after 15 seconds in a small diode-based hand reflectometer (RQflex® reflectometer, Merck KGaA, Darnstadt (Gromes R. Tanzer D., G.I.T. 5 (2001), 2–5)). Tables 1 and 2 show the correlation between the measured relative remissions (%) and the total acid content.

The total acid content of the samples employed is determined using the EC reference method (potentiometric titration).

TABLE 1

Total acid measurement range about 1–8 g/l:

| Total acid [g/l] | % rel. remission |
|---|---|
| 1 | 26 |
| 2 | 32 |
| 3 | 39 |
| 4 | 47 |
| 5 | 55 |
| 6 | 64 |
| 7 | 73 |
| 8 | 81 |

TABLE 2

Total acid measurement range about 7–14 g/l:

| Total acid [g/l] | % rel. remission |
|---|---|
| 7 | 11 |
| 8 | 23 |
| 9 | 33 |
| 10 | 42 |
| 11 | 50 |
| 12 | 58 |
| 13 | 65 |
| 14 | 72 |

Example 2

Practical Test: Determination of Total Acid in Must and Wine Samples Compared with the Reference Method The analysis zones from Example 1 are applied to a test stick. The separation of the two test zones measuring 8×6 mm is 4 mm.

According to the procedure from Example 1, various samples are investigated compared with the reference method, using the correlation between remission and total acid from Example 1 as calibration curve.

The RQflex® reflectometer has a double-lens system necessary for this type of evaluation.

The results are shown in FIG. 1. The total acid content in g/l is plotted on the y axis, and the sample number is plotted on the x axis. The dotted bars plotted on the left for the respective sample number show the analytical result for the respective sample determined using the method according to the invention. The striped bars arranged on the right for the respective sample show the analytical result determined using the reference method.

The invention claimed is:

1. A method for the determination of total acid in must and wine, comprising:
    a) providing a test stick which has at least one pH indicator;
    b) adding an alkaline reagent solution to the sample to be analysed;
    c) dipping the test stick into the mixture from step b);
    d) evaluating a colour reaction of the at least one pH indicator on the test stick to determine total acid,
wherein said alkaline reagent solution is a phosphate buffer, a triethanolamine buffer, a buffer based on a heterocyclic amine or a derivative or mixture thereof.

2. A method according to claim 1, wherein the alkaline reagent solution is a tris(hydroxymethyl)aminomethane buffer.

3. A method according to claim 1, wherein a test stick which comprises, as pH indicator, one or more of the indicators Bromocresol Green, Phenol Red, Bromophenol Red, Chlorophenol Red and curcumine is provided in step a).

4. A method according to claim 1, wherein said test stick has two zones with different pH indicators.

5. A method according to claim 1, wherein the evaluation in step d) is carried out reflectometrically.

6. The method of claim 2, wherein the buffer pH is between about 9–12.5.

7. The method of claim 6, wherein the buffer pH is between about 10–10.5.

* * * * *